United States Patent
Wu et al.

(10) Patent No.: US 9,435,751 B2
(45) Date of Patent: Sep. 6, 2016

(54) REMOTE DETECTION AND IDENTIFICATION OF NUCLEAR MATERIALS USING MULTIPLE ION-CHAMBERS

(71) Applicants: Dong Ho Wu, Olney, MD (US); Benjamin Graber, Washington, DC (US)

(72) Inventors: Dong Ho Wu, Olney, MD (US); Benjamin Graber, Washington, DC (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/720,565

(22) Filed: May 22, 2015

(65) Prior Publication Data

US 2015/0338354 A1 Nov. 26, 2015

Related U.S. Application Data (60) Provisional application No. 62/002,131, filed on May 22, 2014.

(51) Int. Cl.
| | |
|---|---|
| G01N 23/00 | (2006.01) |
| G01N 30/00 | (2006.01) |
| G01V 5/00 | (2006.01) |
| G01T 1/185 | (2006.01) |

(52) U.S. Cl.
CPC .............. *G01N 23/00* (2013.01); *G01N 30/00* (2013.01); *G01T 1/185* (2013.01); *G01V 5/00* (2013.01); *G01V 5/0091* (2013.01)

(58) Field of Classification Search
USPC ................................................ 250/281, 282
See application file for complete search history.

(56) References Cited

U.S. PATENT DOCUMENTS

| | | |
|---|---|---|
| 2012/0024044 A1 | 2/2012 | Tao et al. |
| 2012/0305773 A1 | 12/2012 | Wu et al. |

FOREIGN PATENT DOCUMENTS

| | | |
|---|---|---|
| WO | 2010147681 A2 | 12/2010 |

OTHER PUBLICATIONS

O'Malley, J.; Current Status of AWE Programmes into Stand-off Detection of Special Nuclear Material (SNM); Chemical, Biological, Radiological, Nuclear, and Explosives (CBRNE) Sensing X; Proceedings of SPIE; pp. 1-12; vol. 7304; (May 2009).

*Primary Examiner* — Nicole Ippolito
*Assistant Examiner* — Hanway Chang
(74) *Attorney, Agent, or Firm* — US Naval Research Laboratory; Kerry L. Broome (57) ABSTRACT

A system and method for detecting and identifying nuclear materials by detecting and measuring positive and negative ions in multiple ion chambers, wherein each ion chamber comprises a different gas, including oxygen, argon, nitrogen, carbon dioxide, and humid air, and one or more ion counters. The ion data can be transmitted to an isotope identification module. The ion data can include a distinctive pattern data of positive-ion production rates and negative-ion production rates generated from the measured positive and negative ions. The isotope identification module can compare the pattern data of positive-ion production rates and negative-ion production rates to an isotope data library, and identify a detected nuclear isotope with the isotope identification module. A display can show the identified detected nuclear isotope; a probability of the presence of the detected nuclear isotope; and a radioactivity of the detected nuclear isotope.

12 Claims, 12 Drawing Sheets

| Isotope | Calculated Current Activity (uCi) | Distance to Ion Counters (cm) | Calculated Dose Rate (uR/hr) |
|---|---|---|---|
| Am-241 | 74.81 | 5 | 502 |
| Ba-133 | 62.55 | 5 | 6005 |
| Cs-137 | 70.40 | 5 | 9678 |
| Co-60 | 51.98 | 5 | 38900 |
| Na-22 | 36.03 | 5 | 35586 |

REMOTE DETECTION AND IDENTIFICATION OF NUCLEAR MATERIALS USING MULTIPLE ION-CHAMBERS

CROSS-REFERENCE TO RELATED APPLICATIONS

This application claims priority to provisional patent application entitled, "SYSTEM AND METHOD OF REMOTE DETECTION AND IDENTIFICATION OF NUCLEAR MATERIALS USING MULTIPLE ION-CHAMBERS," filed on May 22, 2014, and assigned U.S. Application No. 62/002,131; the entire contents of which are hereby incorporated by reference.

FIELD OF THE INVENTION

The present invention relates generally to the detection of nuclear materials, and more specifically, it relates to the detection and identification of hidden nuclear materials, including hidden Special Nuclear Materials (SNM), at a standoff distance.

BACKGROUND

There are some prior art methods for detecting and identifying hidden nuclear materials. The most notable technique utilizes a gamma-ray spectrometer to measure the gamma-ray spectrum, and the system consists of a high-sensitivity gamma-ray detector made of high purity germanium (or lithium or other material) and a multi-channel analyzer. For a relatively high-sensitivity gamma-ray spectrometer, the gamma-ray detector is typically cooled by a cryogenic liquid (mostly liquid nitrogen), and the detector must be carefully handled since it can be easily damaged. In addition, the spectrometer is expensive to procure and operate as it constantly requires cryogenic liquid, and it is too delicate to operate by a layperson. Furthermore, the gamma-ray spectrometer is not sensitive enough to detect an isotope at a long distance.

In another prior art method, a system uses a single chamber to detect a nuclear material; however, this method does not allow the identification of the type of nuclear material detected.

Other techniques of detecting and identifying hidden nuclear material include the acoustic technique, the thermal imaging technique, and the air-fluorescence technique. Each of these techniques has been investigated by many other research groups, and all have proved to be unreliable. In addition, active detection techniques, such as active neutron techniques and the use of high-energy electromagnetic showers, including high-energy protons and active gamma techniques, are not safe to operate and can be very expensive.

Accordingly, there remains a need in the art for a system and method of detecting and identifying remote nuclear material at a standoff distance, which is more accurate than prior art systems and easier and less expensive to operate.

SUMMARY OF THE INVENTION

According to one aspect of the invention, a nuclear material detection and identification system is described that includes multiple ion chambers that can be configured to detect and measure positive and negative ions in the multiple ion chambers, wherein each ion chamber comprises a different gas and one or more ion counters. An isotope data library can be configured to store positive and negative ion production patterns of various isotopes for different gas environments. An isotope identification module can be configured to receive a plurality of ion data from the plurality of ion chambers, wherein the plurality of ion data comprises distinctive pattern data of positive-ion production rates and negative-ion production rates generated from the measured positive and negative ions. Furthermore, the isotope identification module can be configured to compare the pattern data of positive-ion production rates and negative-ion production rates to the isotope data library to identify a detected nuclear isotope.

According to another aspect of the invention, a method is described for detecting and measuring positive and negative ions in multiple ion chambers, wherein each ion chamber comprises a different gas and one or more ion counters. Next, ion data can be transmitted to an isotope identification module, wherein the ion data includes distinctive pattern data of positive-ion production rates and negative-ion production rates generated from the measured positive and negative ions. Finally, the pattern data of positive-ion production rates and negative-ion production rates can be compared to an isotope data library to identify a detected nuclear isotope with the isotope identification module.

These and other aspects, objects, and features of the present invention will become apparent from the following detailed description of the exemplary embodiments, read in conjunction with, and reference to, the accompanying drawings.

BRIEF DESCRIPTION OF THE DRAWINGS

The following description and drawings set forth certain illustrative implementations of the disclosure in detail, which are indicative of several exemplary ways in which the various principles of the disclosure may be carried out. The illustrated examples, however, are not exhaustive of the many possible embodiments of the disclosure. Other objects, advantages and novel features of the disclosure will be set forth in the following detailed description of the disclosure when considered in conjunction with the drawings, in which.

DETAILED DESCRIPTION OF EXEMPLARY EMBODIMENTS

One or more embodiments or implementations are hereinafter described in conjunction with the drawings, where like reference numerals refer to like elements throughout, and where the various features are not necessarily drawn to scale.

Figure 1:
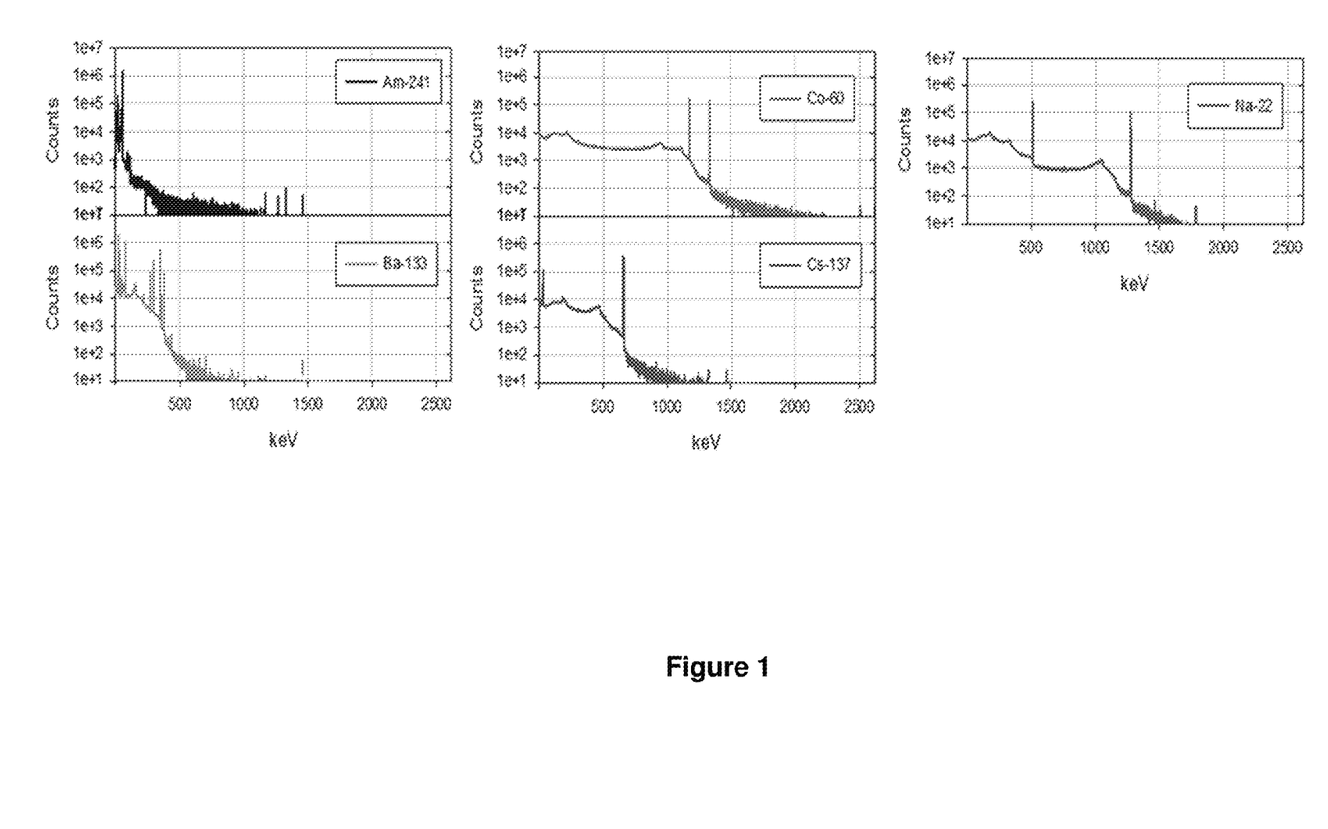
FIG. 1 is a gamma-ray energy spectra of five different isotopes.

FIG. 1 is a gamma-ray energy spectra of five different isotopes. One of ordinary skill in the art knows that gamma-ray radiation interacts with gas molecules and produces positive and negative ions. Each gas species has a different ionization energy, and the gas molecules have different cross sections for interacting with the gamma-ray radiation. A nuclear isotope produces gamma radiation with a characteristic spectrum, as can be seen in FIG. 1. Specifically, FIG. 1 illustrates Gamma-ray energy spectra of isotopes Am-241, Ba-133, Co-60, Cs-137 and Na-22.

Therefore, when the gamma radiation interacts with a specific gas molecule, the positive and negative ion-production rates uniquely depend on the gamma energies and the gas species. In an exemplary embodiment of the invention, multiple different gas chambers, including oxygen gas, argon gas, nitrogen gas, carbon dioxide gas, and humid air, can be exposed to nuclear radiation produced by a given isotope, and then the positive and negative ion-production rate in the multiple different gas environments can be measured. In an exemplary embodiment of the invention, different isotopes, including Am241, Ba133, Cs137, Co60, Na22, Pu239 and U235 can be used. One of ordinary skill in the art will understand that other types of gas environments and other isotopes could also be utilized.

Figure 2A:
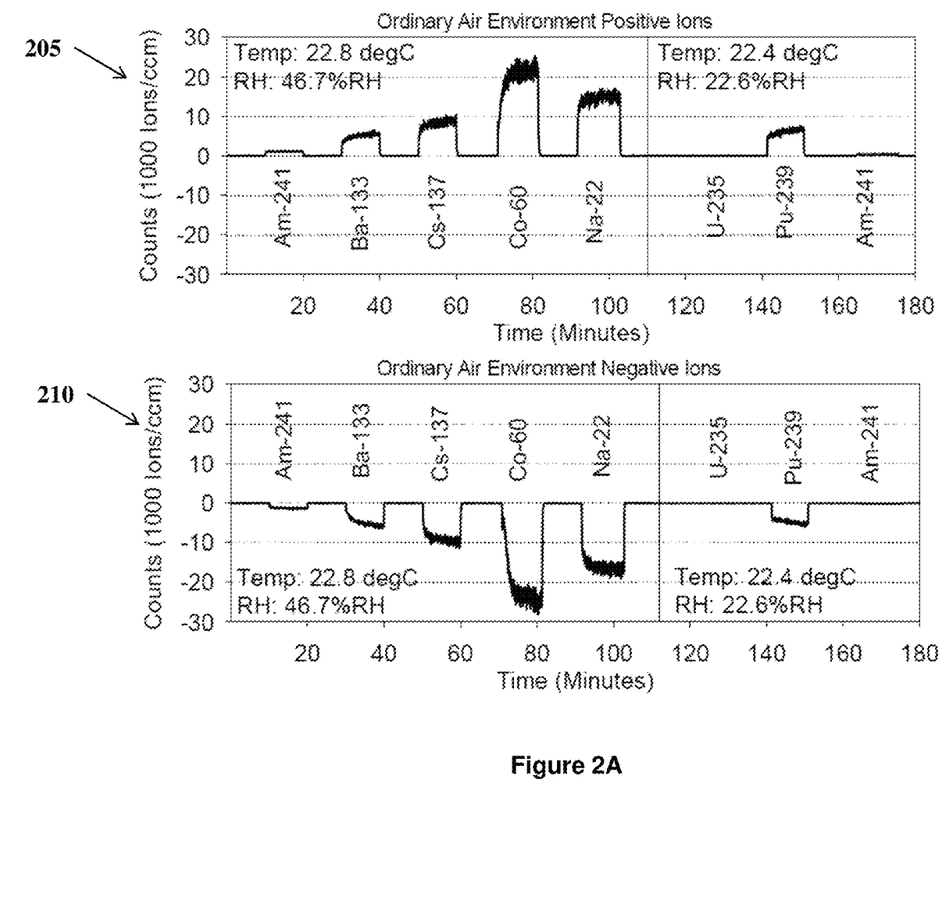
FIG. 2A is a graph of positive and negative ion counts of different isotopes in a chamber containing ordinary air with 46.7% relative humidity, in accordance with an exemplary embodiment of the invention.
Figure 2B:
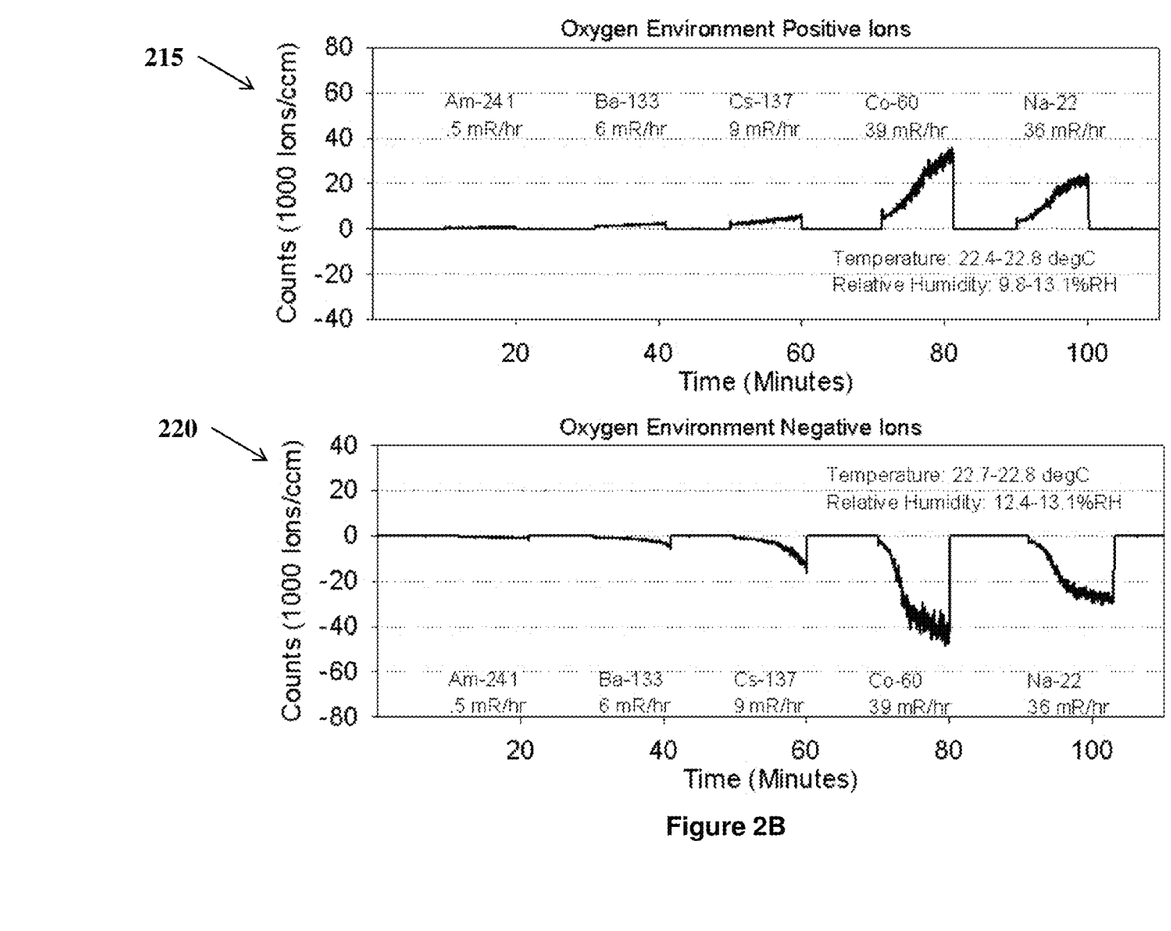
FIG. 2B is a graph of positive and negative ion counts of different isotopes in a chamber containing oxygen gas, in accordance with an exemplary embodiment of the invention.
Figure 2C:
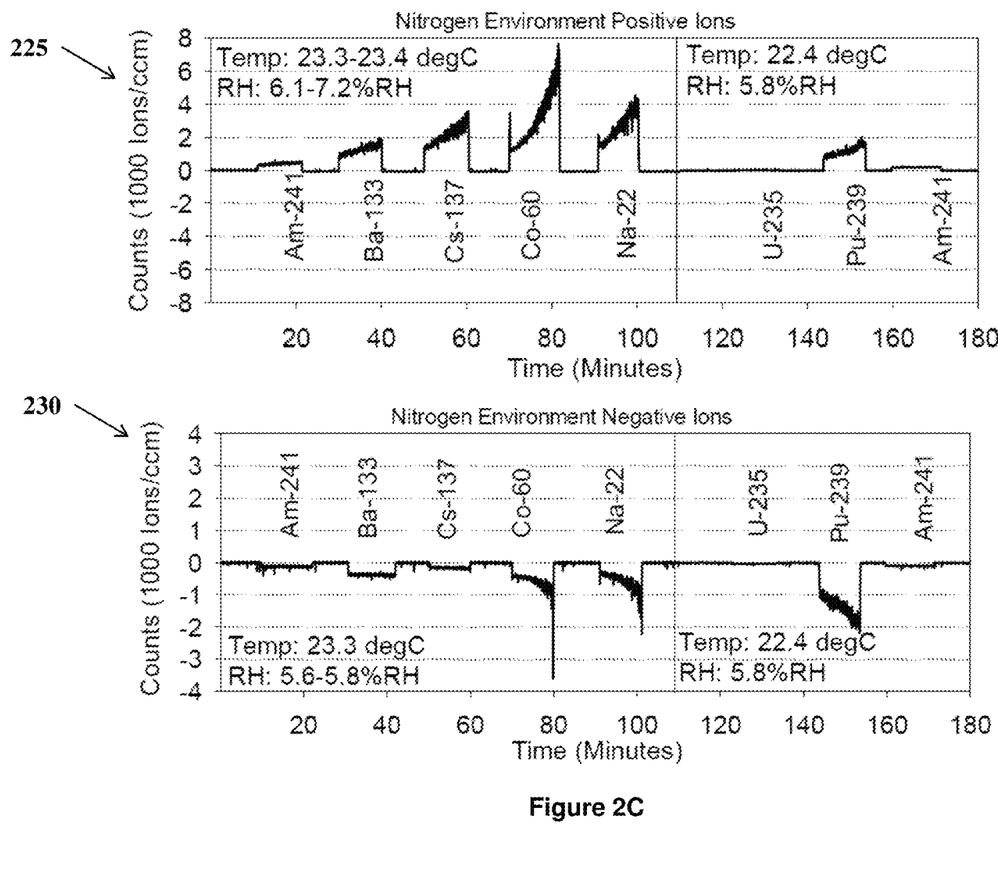
FIG. 2C is a graph of positive and negative ion counts of different isotopes in a chamber containing nitrogen gas, in accordance with an exemplary embodiment of the invention.
Figure 2D:
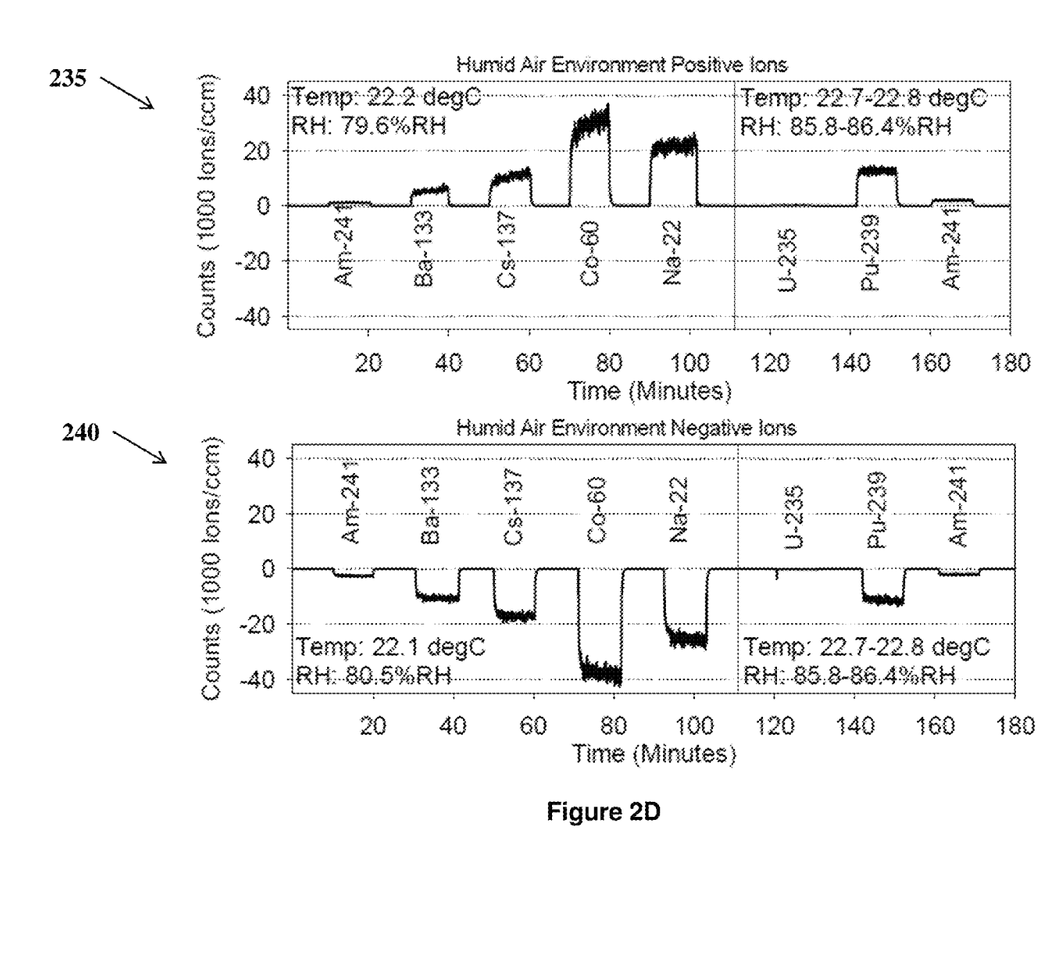
FIG. 2D is a graph of positive and negative ion counts of different isotopes in a chamber containing humid air (79.6% R.H.), in accordance with an exemplary embodiment of the invention.
Figure 2E:
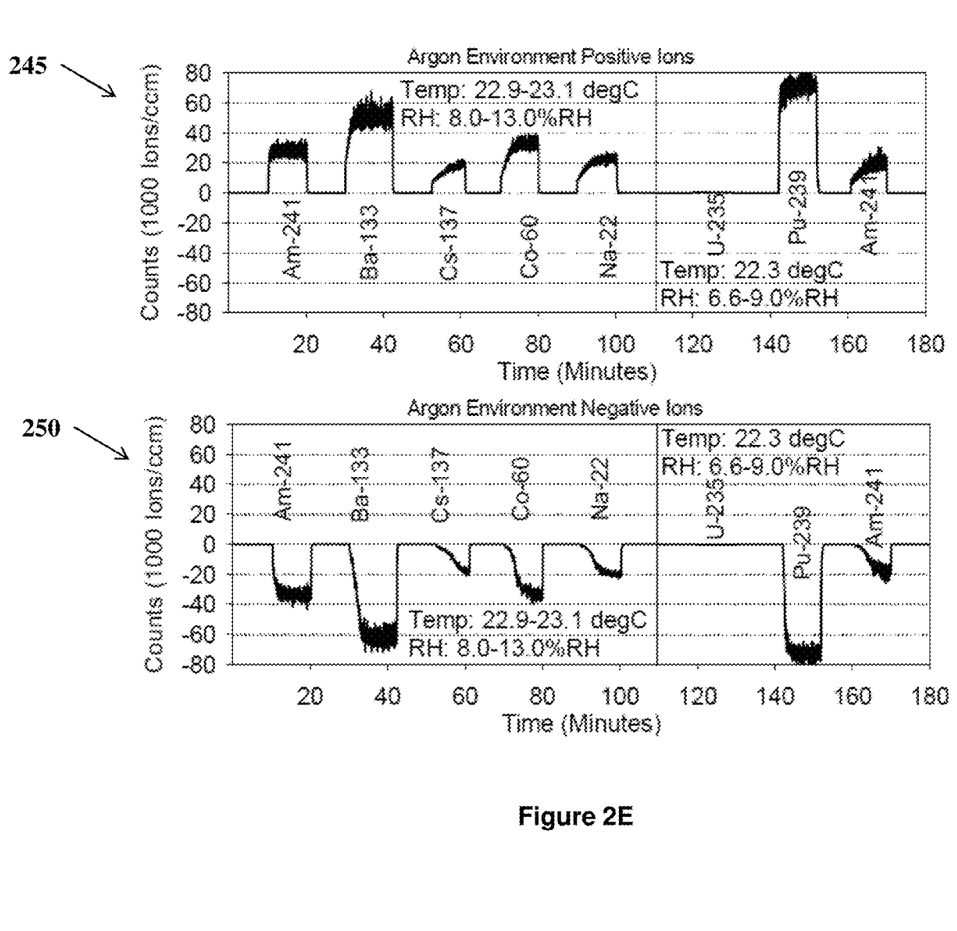
FIG. 2E is a graph of positive and negative ion counts of different isotopes in a chamber containing argon gas, in accordance with an exemplary embodiment of the invention.
Figure 2F:
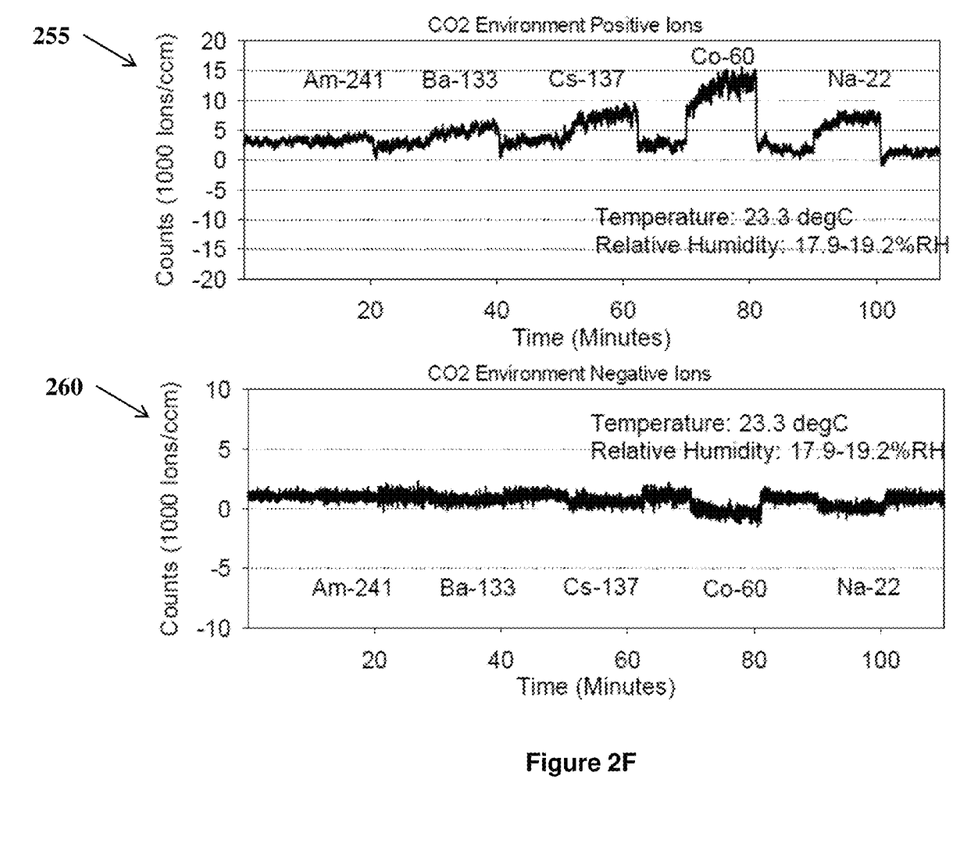
FIG. 2F is a graph of positive and negative ion counts of different isotopes in a chamber containing carbon dioxide gas, in accordance with an exemplary embodiment of the invention.

FIG. 2A through FIG. 2F represent graphs of positive and negative ion counts of different isotopes in different gas environments, in accordance with an exemplary embodiment of the invention. Specifically, FIG. 2A is a graph of positive ion 205 and negative ion 210 counts of different isotopes in a chamber containing ordinary air with 46.7% relative humidity, in accordance with an exemplary embodiment of the invention. FIG. 2B is a graph of positive ion 215 and negative ion 220 counts of different isotopes in a chamber containing oxygen gas. FIG. 2C is a graph of positive ion 225 and negative ion 230 counts of different isotopes in a chamber containing nitrogen gas. FIG. 2D is a graph of positive ion 235 and negative ion 240 counts of different isotopes in a chamber containing humid air (79.6% R.H.). FIG. 2E is a graph of positive ion 245 and negative ion 250 of different isotopes in a chamber containing argon gas. FIG. 2F is a graph of positive ion 255 and negative ion 260 counts of different isotopes in a chamber containing carbon dioxide gas.

As indicated by FIGS. 2A through 2F it becomes apparent that: (1) the positive and negative ion-production rates are remarkably dependent on the gas environment, as well as on the type of isotope; (2) the temporal patterns of the positive and negative ion-production rates in a few gases (e.g., nitrogen, oxygen and argon) are quite distinguishable from those of ordinary air; and (3) argon gas seems to produce ions more efficiently, when it is exposed to low-energy gamma rays (e.g., gamma-rays from Am241, Ba133 and Pu239).

Figure 3:
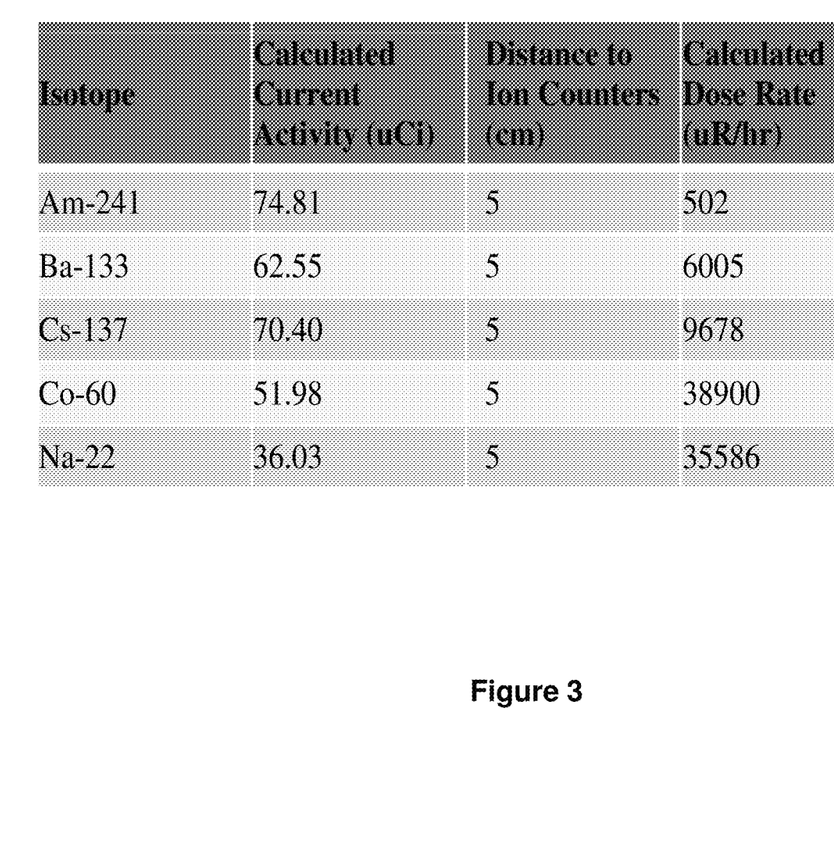
FIG. 3 is a table that shows the radioactivities and the calculated dose rates for different isotopes, in accordance with an exemplary embodiment of the invention.

FIG. 3 is a table that shows the radioactivities and the calculated dose rates for different isotopes, in accordance with an exemplary embodiment of the invention. When dose rates and ion production rates are compared, as represented in FIGS. 2A through 2F, the higher dose rate typically correlates with the larger ion-production rate in most gases, except for Argon gas. In earlier experiments, results using $CO_2$ gas were not very reliable, as they fluctuated uncontrollably. However, recent experiments indicate that $CO_2$ can produce reliable and stable results as well; therefore, an exemplary multi ion chamber system can utilize $CO_2$, ordinary air, Argon, and Oxygen gases, and can detect and identify an isotope at a long standoff distance. One of ordinary skill in the art will understand that other gases can potentially be used as well.

Figure 4:
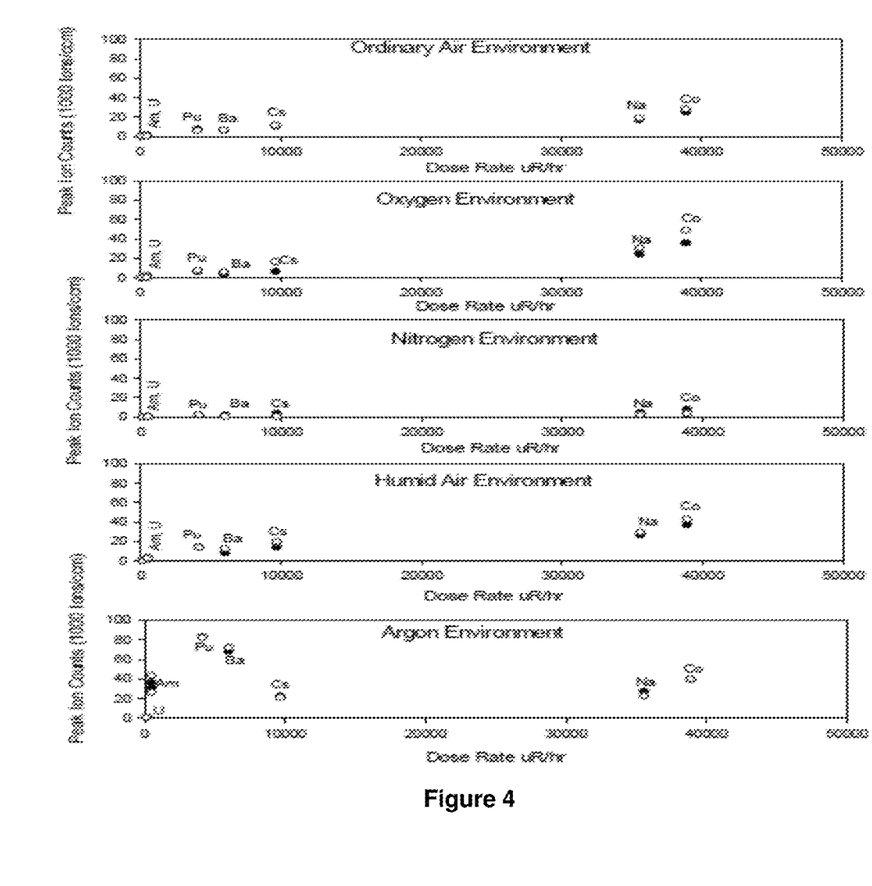
FIG. 4 is a chart that shows the relationship between the dose rate and the ion production rate for different gas environments, in accordance with an exemplary embodiment of the invention.

FIG. 4 is a chart that shows the relationship between the dose rate and the ion production rate for different gas environments, in accordance with an exemplary embodiment of the invention. Specifically, in FIG. 4, the positive ion count is represented by a black solid circle, and the negative ion count is represented by an open circle. The ion counts represented are produced by Am-241, U-235, Pu-239, Ba-133, Cs-137, Na-22 and Co-60 isotopes in several different gas environments are illustrated. While the radioactivities of the isotopes are within the range from 20 μCi to 75 μCi, their dose rates at a distance of 5 cm spread over the range from 500 μR/hr to 39,000 μR/hr. One of ordinary skill in the art can see that the ion production rate is related not only to the dose rate but also to the gamma-energy spectra of the isotopes. Furthermore, referring to FIG. 4, additional relationships are represented. For example, for the same dose rate, the lower the gamma-energy spectrum the isotope has the more ions it tends to produce. Specifically, among the isotopes used and represented in FIG. 4, Am241 has the lowest gamma-energy spectrum, with the major gamma-ray energy peak at about 59.54 KeV. Accordingly, it also produces considerably more ions than any of the other isotopes for the effective dose rate of 50 mR/hr. Similar trends can also be found for Pu239, Ba133, and Cs137, which have some low-energy gamma-ray spectra. Another relationship represented in FIG. 4 is that each isotope produces distinctive positive and negative ion-production-patterns for different gas environments.

Figure 5:
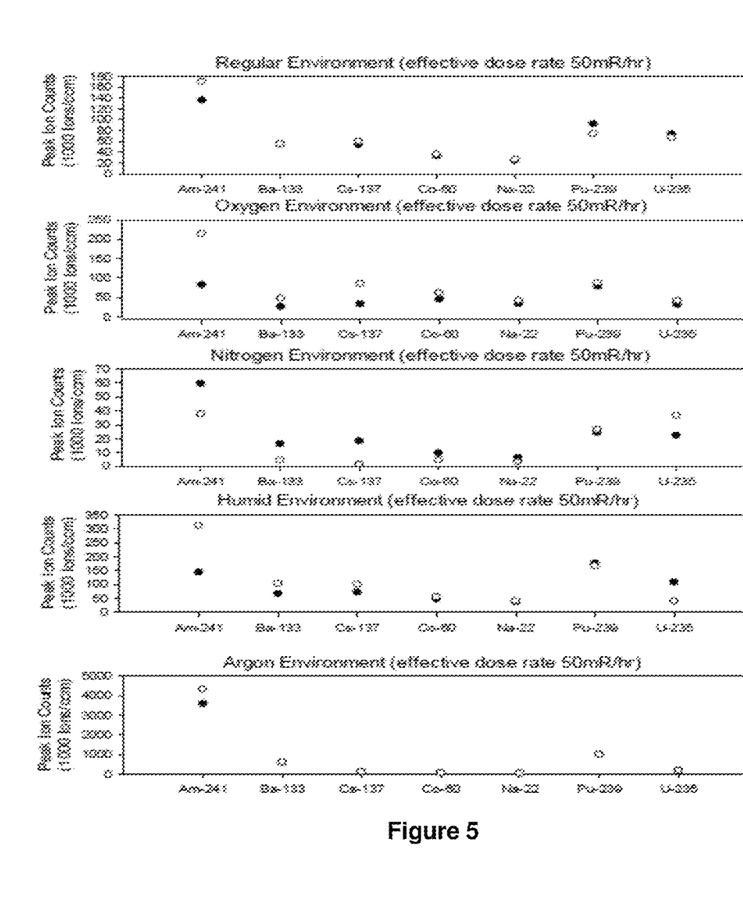
FIG. 5 is a chart that shows the relationship between the dose rate and the ion production rate for different gas environments when the ion production rate is normalized for the effective dose rate of 50 mR/hr, in accordance with an exemplary embodiment of the invention.

FIG. 5 is a chart that shows the relationship between the dose rate and the ion production rate for different gas environments when the ion production rate is normalized for the effective dose rate of 50 mR/hr, in accordance with an exemplary embodiment of the invention. Specifically, FIG. 5 shows positive ion counts represented by black solid circles and negative ion counts represented by open circles for Am-241, Ba-133, Cs-137, Co-60, Na-22, Pu-239 and U-235 isotopes with effective dose rate of 50 mR/hr.

Figure 6:
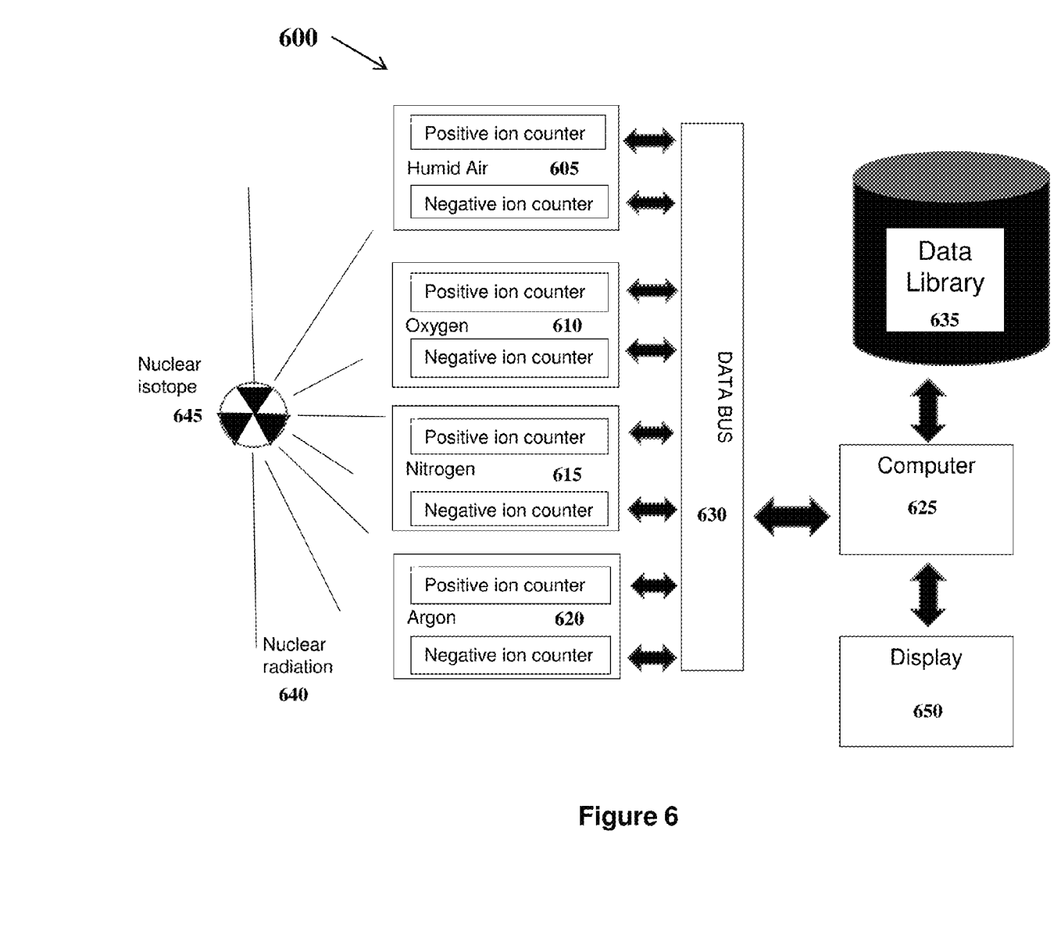
FIG. 6 is a schematic of a standoff nuclear material detection and identification system, based on a multiple ion-counting chamber technique, in accordance with an exemplary embodiment of the invention.

FIG. 6 is a block diagram of a standoff nuclear material detection and identification system 600, based on a multiple ion-counting chamber technique, in accordance with an exemplary embodiment of the invention. FIG. 6 shows that by utilizing positive and negative ion production patterns in different gas environments, detection and identification of a given nuclear isotope at a standoff distance can be repeatedly achieved. In an exemplary embodiment of the invention, multiple ion chambers can be configured to detect and measure positive and negative ions in the multiple ion chambers. Each of the multiple ion chambers can include a different gas, such as oxygen, argon, nitrogen, carbon dioxide, and humid air; and one or more ion counters (e.g., a positive ion counter and a negative ion counter).

In FIG. 6, the four ion-chambers 605, 610, 615, and 620, each have at least two ion counters (i.e., positive and negative ion counters) in each chamber that can detect positive and negative ions simultaneously. One of ordinary skill in the art will understand that less than or more than four ion chambers can be utilized in the exemplary system. Furthermore, one of ordinary skill in the art will understand that more or less than two ion counters can be utilized for each ion chamber in the exemplary system, with the number of ion counters only limited by cost and space constraints. In an exemplary embodiment of the invention, each ion-chamber can be separately interfaced to a special computer system 625 via a data-communications bus 630. The computer system 625 can include instructions stored in a machine-readable medium and a processor that executes the instructions. When the standoff nuclear material detection and identification system 600 is in operation, the computer system 625 can operate to collect, compare, measure, and analyze data to identify any given isotope under examination.

As noted, in an exemplary embodiment of the invention, the system 600 can include at least two ion counters for each chamber, and then can be configured to operate to measure the detected positive and the negative ions simultaneously. When the multiple ion-chambers 605, 610, 615, and 620, each of them containing different gases, are exposed to nuclear radiation 640 from a nuclear isotope(s) 645, they can produce very distinctive pattern data of positive-ion production rates and negative-ion production rates generated from the measured positive and negative ions. This pattern data, or ion data, can be collected from each ion chamber and can be transferred via a data communications bus 630 to the computer system 625. The computer system 625 can include an isotope identification module (not pictured), which can be implemented in the computer system that comprises instructions stored in a machine-readable medium and a processor that executes the instructions. Furthermore, the computer system 625 can include, or be separately connected to, a data library 635. The data library 635 can include a data library of positive and negative of ion production patterns of various isotopes for different gas environments.

In an exemplary embodiment of the invention, when the isotope identification module in the computer system 625 receives the ion data, then the isotope identification module can compare the pattern data of positive-ion production rates and negative-ion production rates to the data in the isotope data library 635. Therefore, by comparing a ratio of positive- and negative-ion numbers and temporal patterns of the ion production rates, the isotope identification module can identify the type of a given nuclear isotope that has been detected and measured by the ion counters. Additionally, the isotope identification module can estimate the radioactivity of the nuclear isotope 645 that has been detected, as well as estimate the probability of the presence of the detected nuclear isotope.

More specifically, the isotope identification module can be a support vector machine (SVM) that commonly used in pattern recognition, bioinformatics, image sorting, and data analytics. The isotope identification module can include a learning algorithm is configured to identify the isotopes. The goal of the isotope identification module is to classify, or identify, test data using a set of vectors that it assigns based on previously processed training data. To accomplish this, the data library 635 can be used as training data for the isotope identification module. The isotope identification module can analyze the training data and systematically determine a set of lines that divide the data into each "class." In an exemplary embodiment of the invention, these classes are the isotopes and the dividing lines are stored as "vectors." The test data will fall on one side or another of these vectors, which will determine what class the isotope identification module will assign to that test data. In an exemplary embodiment of the invention, a particular SVM method utilized by the isotope identification module is a GMNPSVM classifier with a real polynomial kernel of 10 or 20 degrees that assumes inhomogeneous data distribution and uses normalization. One of ordinary skill in the art will understand that other SVM methods can be utilized.

Figure 7:
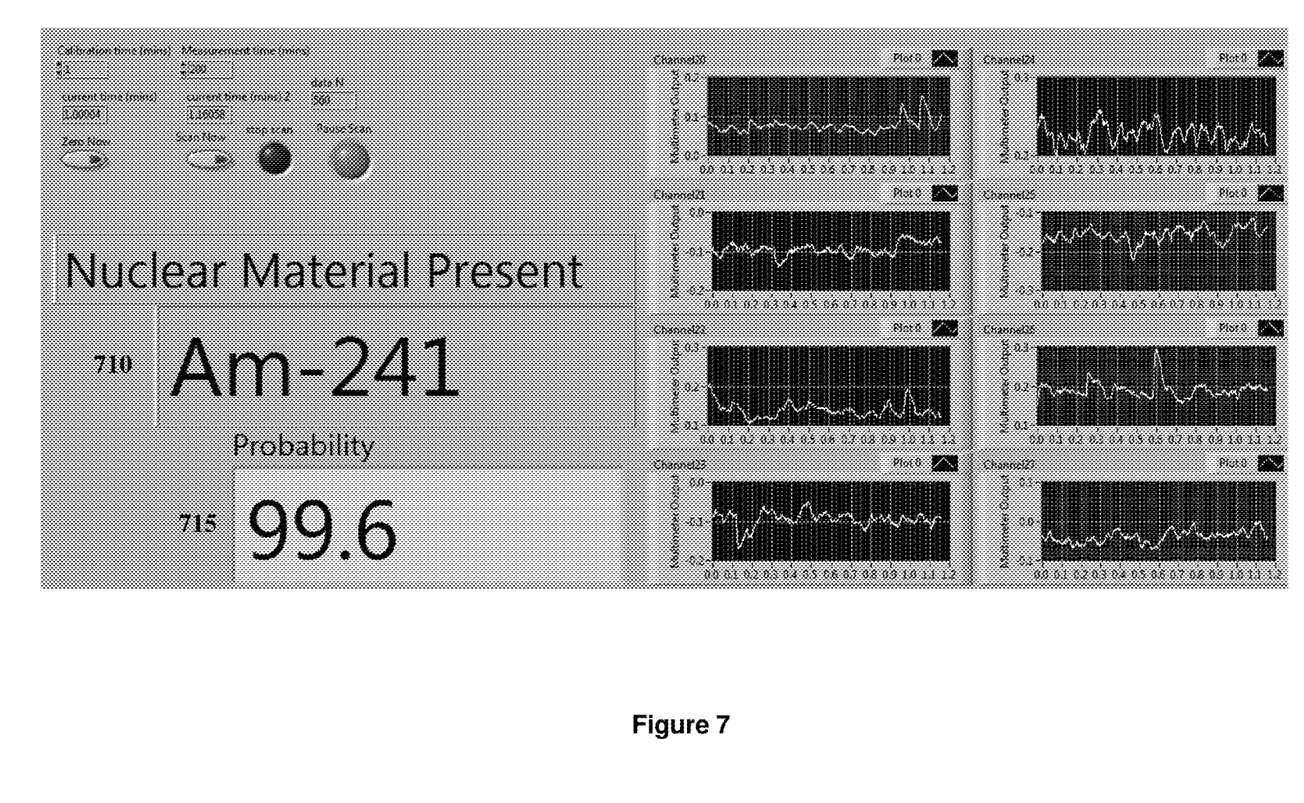
FIG. 7 is an example display of a standoff nuclear material detection and identification system, in accordance with an exemplary embodiment of the invention.

FIG. 7 is an example display 650 of a standoff nuclear material detection and identification system, in accordance with an exemplary embodiment of the invention. The display 650 can be connected to the computer system 625, or be a separate component. The display 650 can be configured to display, or show, multiples types of information regarding the detected isotope information (i.e., "detected nuclear isotope information"). The detected nuclear isotope information can include the type of identified detected nuclear isotope 710; a probability of the presence of the detected nuclear isotope 710; and a radioactivity of the detected nuclear isotope (not shown in FIG. 7). One of ordinary skill in the art will understand that other types of detected nuclear isotope information can also be displayed.

In an exemplary embodiment of the invention described herein and illustrated in FIG. 6, the standoff nuclear material detection and identification system 600 can detect, measure, and identify nuclear isotopes in a wide range of short and long distances. For example, the system can operate, detect, measure, and identify nuclear isotopes at a wide range of between about 0.3 meters up to about 110 meters and more. One of ordinary skill in the art will understand that distances greater than or less than that range can also be realized. Furthermore, the exemplary system 600 can also be relatively inexpensive, and personnel without special training can operate the exemplary system 600.

Portions of the invention can comprise a computer program that embodies the functions described herein. Furthermore, any modules described herein, such as the isotope identification module, can be implemented in a computer system that comprises instructions stored in a machine-readable medium and a processor that executes the instructions. However, it should be apparent that there could be many different ways of implementing the invention in computer programming, and the invention should not be construed as limited to any one set of computer program instructions. Further, a skilled programmer would be able to write such a computer program to implement an exemplary embodiment based on the figures and associated description in the application text. Therefore, disclosure of a particular set of program code instructions is not considered necessary for an adequate understanding of how to make and use the invention.

It should be understood that the foregoing relates only to illustrative embodiments of the present invention, and that numerous changes may be made therein without departing from the scope and spirit of the invention as defined by the following claims.

The invention claimed is:

1. A method for detecting and identifying nuclear materials; comprising the steps of:
   detecting and measuring positive and negative ions in a plurality of ion chambers, wherein each ion chamber comprises a different gas and one or more ion counters;
   transmitting a plurality of ion data to an isotope identification module; wherein the plurality of ion data comprises distinctive pattern data of positive-ion production rates and negative-ion production rates generated from the measured positive and negative ions, wherein the isotope identification module is implemented in a computer system that comprises instructions stored in a machine-readable medium and a processor that executes the instructions; and
   comparing the pattern data of positive-ion production rates and negative-ion production rates to an isotope data library and identifying a detected nuclear isotope with the isotope identification module.

2. The method of claim 1, further comprising the step of estimating the radioactivity of the detected nuclear isotope with the isotope identification module.

3. The method of claim 1, further comprising the step of estimating the probability of the presence of the detected nuclear isotope with the isotope identification module.

4. The method of claim 1, wherein the step of detecting and measuring positive and negative ions in a plurality of ion chambers comprises counting the positive and negative ions in each ion counter in each ion chamber, and calculating a ion production rate for each ion chamber, wherein the ion production rate is a ratio between the ion count and a radioactivity strength.

5. The method of claim 1, wherein the step of comparing the pattern data of positive-ion production rates and negative-ion production rates to an isotope data library comprises comparing the pattern data of positive-ion production rates and negative-ion production rates generated from the measured positive and negative ions to the isotope data library that comprises a database of positive and negative ion production patterns of various isotopes for different gas environments.

6. The method of claim 1, further comprising the step of displaying detected nuclear isotope information, wherein the detected nuclear isotope information comprises the identified detected nuclear isotope, a probability of the presence of the detected nuclear isotope, and a radioactivity of the detected nuclear isotope.

7. A nuclear material detection and identification system, comprising:
   a plurality of ion chambers each configured to detect and measure positive and negative ions, wherein each ion chamber comprises a different gas and one or more ion counters;
   an isotope data library configured to store positive and negative ion production patterns of various isotopes for different gas environments; and
   an isotope identification module configured to receive a plurality of ion data from the plurality of ion chambers, wherein the plurality of ion data comprises distinctive pattern data of positive-ion production rates and negative-ion production rates generated from the measured positive and negative ions; and further configured to compare the pattern data of positive-ion production rates and negative-ion production rates to the isotope data library to identify a detected nuclear isotope, wherein the isotope identification module is implemented in a computer system that comprises instructions stored in a machine-readable medium and a processor that executes the instructions.

8. The system of claim 7, wherein the different gases comprise oxygen, argon, nitrogen, carbon dioxide, and humid air.

9. The system of claim 7, further comprising a display configured to show a plurality of detected isotope information.

10. The system of claim 9, wherein the plurality of detected nuclear isotope information comprises the identified detected nuclear isotope; a probability of the presence of the detected nuclear isotope; and a radioactivity of the detected nuclear isotope.

11. The system of claim 7, wherein the isotope identification module is further configured to estimate the radioactivity of the detected nuclear isotope and of estimate the probability of the presence of the detected nuclear isotope with the isotope identification module.

12. The system of claim 7, wherein the one or more ion counters in each ion chamber comprise a positive ion counter and negative ion counter.

* * * * *